(12) United States Patent
Tower et al.

(10) Patent No.: US 8,858,619 B2
(45) Date of Patent: Oct. 14, 2014

(54) SYSTEM AND METHOD FOR IMPLANTING A REPLACEMENT VALVE

(75) Inventors: Allen J. Tower, North Lawrence, NY (US); Philipp Bonhoeffer, Paris (FR); Michael L. Martin, Nicholville, NY (US)

(73) Assignee: Medtronic, Inc., Minneapolis, MN (US)

( * ) Notice: Subject to any disclaimer, the term of this patent is extended or adjusted under 35 U.S.C. 154(b) by 469 days.

(21) Appl. No.: 11/432,838

(22) Filed: May 12, 2006

(65) Prior Publication Data

US 2006/0206192 A1     Sep. 14, 2006

Related U.S. Application Data (62) Division of application No. 10/127,969, filed on Apr. 23, 2002, now Pat. No. 8,721,713.

(51) Int. Cl.
| | | |
|---|---|---|
| *A61F 2/24* | (2006.01) | |
| *A61F 2/958* | (2013.01) | |
| *A61F 2/90* | (2013.01) | |

(52) U.S. Cl.
CPC .............. *A61F 2/2433* (2013.01); *A61F 2/2412* (2013.01); *A61F 2/958* (2013.01); *A61F 2/2475* (2013.01); *A61F 2/90* (2013.01)
USPC ...................................................... 623/2.11

(58) Field of Classification Search
USPC ........... 623/1.11, 2.11, 1.24, 1.25, 1.13, 1.14, 623/1.12, 1.23; 604/104, 194, 103.02, 604/103.09; 606/108
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |

(Continued)

FOREIGN PATENT DOCUMENTS

| | | |
|---|---|---|
| DE | 36 40 745 | 6/1987 |
| DE | 195 32 846 | 3/1997 |

(Continued)

OTHER PUBLICATIONS

Huber, et al., "Do Valved Stents Compromise Coronary Flow?" Eur. J. Cardiothorac. Surg. 2004;25:754-759.

(Continued)

*Primary Examiner* — Ryan Severson (57) ABSTRACT

A system for percutaneously inserting a prosthesis containing a biological replacement for a defective valve into an implantation site through a body lumen. The system contains a balloon catheter upon which a collapsable stent containing a venous valvular replacement is mounted. A protective shield is slidably mounted upon the catheter that is movable between a closed position over the balloon and an open position wherein the balloon can be inflated to expand the stent. A central lumen runs through the catheter that is formed of stainless steel. The central lumen provides a one to one torque ratio between the proximal end of the catheter and the distal end to enhance the steerability of the catheter. The vein of the replacement is reduced in thickness between 50% and 90% of its original size thereby considerably reducing the size of the replacement package when the stem is collapsed upon the balloon of the catheter.

17 Claims, 2 Drawing Sheets

(56) References Cited

U.S. PATENT DOCUMENTS

| | | | |
|---|---|---|---|
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,233,690 A | 11/1980 | Akins | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,425,908 A | 1/1984 | Simon | |
| 4,470,157 A | 9/1984 | Love | |
| 4,501,030 A | 2/1985 | Lane | |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,612,011 A | 9/1986 | Kautzky | |
| 4,647,283 A | 3/1987 | Carpentier et al. | |
| 4,648,881 A | 3/1987 | Carpentier et al. | |
| 4,655,771 A | 4/1987 | Wallsten | |
| 4,662,885 A | 5/1987 | DiPisa, Jr. | |
| 4,665,906 A | 5/1987 | Jervis | |
| 4,681,110 A | 7/1987 | Wiktor | |
| 4,710,192 A | 12/1987 | Liotta et al. | |
| 4,733,665 A | 3/1988 | Palmaz | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,954,126 A | 9/1990 | Wallsten | |
| 4,966,604 A | 10/1990 | Reiss | |
| 4,967,743 A | 11/1990 | Lambert | |
| 4,979,939 A | 12/1990 | Shiber | |
| 4,986,830 A | 1/1991 | Owens et al. | |
| 4,994,077 A | 2/1991 | Dobben | |
| 5,002,559 A | 3/1991 | Tower | |
| 5,007,896 A | 4/1991 | Shiber | |
| 5,026,366 A | 6/1991 | Leckrone | |
| 5,047,041 A | 9/1991 | Samuels | |
| 5,059,177 A | 10/1991 | Towne et al. | |
| 5,061,273 A | 10/1991 | Yock | |
| 5,085,635 A | 2/1992 | Cragg | |
| 5,089,015 A | 2/1992 | Ross | |
| 5,152,771 A | 10/1992 | Sabbaghian et al. | |
| 5,161,547 A | 11/1992 | Tower | |
| 5,163,953 A | 11/1992 | Vince | |
| 5,167,628 A | 12/1992 | Boyles | |
| 5,217,483 A | 6/1993 | Tower | |
| 5,232,445 A | 8/1993 | Bonzel | |
| 5,257,979 A | 11/1993 | Jagpal | |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum et al. | |
| 5,338,313 A | 8/1994 | Mollenauer et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,429,597 A | 7/1995 | DeMello et al. | |
| 5,431,676 A | 7/1995 | Dubrul et al. | |
| 5,443,446 A | 8/1995 | Shturman | |
| 5,449,372 A | 9/1995 | Schmaltz et al. | |
| 5,480,424 A | 1/1996 | Cox | |
| 5,496,346 A | 3/1996 | Horzewski et al. | |
| 5,500,014 A | 3/1996 | Quijano et al. | |
| 5,507,767 A | 4/1996 | Maeda et al. | |
| 5,514,109 A | 5/1996 | Mollenauer et al. | |
| 5,545,209 A | 8/1996 | Roberts et al. | |
| 5,545,211 A | 8/1996 | An et al. | |
| 5,554,185 A | 9/1996 | Block et al. | |
| 5,556,387 A | 9/1996 | Mollenauer et al. | |
| 5,575,818 A | 11/1996 | Pinchuk | |
| 5,580,922 A | 12/1996 | Park et al. | |
| 5,591,195 A | 1/1997 | Taheri et al. | |
| 5,597,378 A | 1/1997 | Jervis | |
| 5,609,626 A | 3/1997 | Quijano et al. | |
| 5,643,278 A * | 7/1997 | Wijay | 623/1.11 |
| 5,645,559 A | 7/1997 | Hachtman et al. | |
| 5,667,523 A | 9/1997 | Bynon et al. | |
| 5,674,277 A | 10/1997 | Freitag | |
| 5,683,451 A | 11/1997 | Lenker et al. | |
| 5,695,498 A | 12/1997 | Tower | |
| 5,702,368 A | 12/1997 | Stevens et al. | |
| 5,713,953 A | 2/1998 | Vallana et al. | |
| 5,749,890 A | 5/1998 | Shaknovich | |
| 5,749,921 A | 5/1998 | Lenker et al. | |
| 5,782,809 A | 7/1998 | Umeno et al. | |
| 5,800,456 A | 9/1998 | Maeda et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,840,081 A | 11/1998 | Andersen et al. | |
| 5,855,597 A | 1/1999 | Jayaraman | |
| 5,855,601 A | 1/1999 | Bessler et al. | |
| 5,860,966 A | 1/1999 | Tower | |
| 5,861,028 A | 1/1999 | Angell | |
| 5,868,783 A | 2/1999 | Tower | |
| 5,876,448 A | 3/1999 | Thompson et al. | |
| 5,888,201 A | 3/1999 | Stinson et al. | |
| 5,891,191 A | 4/1999 | Stinson | |
| 5,906,606 A * | 5/1999 | Chee et al. | 604/527 |
| 5,906,619 A | 5/1999 | Olson et al. | |
| 5,907,893 A | 6/1999 | Zadno-Azizi et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A * | 9/1999 | Leonhardt et al. | 623/1.24 |
| 5,968,068 A | 10/1999 | Dehdashtian et al. | |
| 5,984,957 A | 11/1999 | Laptewicz, Jr. et al. | |
| 5,997,573 A | 12/1999 | Quijano et al. | |
| 6,022,370 A | 2/2000 | Tower | |
| 6,027,525 A | 2/2000 | Suh et al. | |
| 6,042,589 A | 3/2000 | Marianne | |
| 6,042,598 A | 3/2000 | Tsugita et al. | |
| 6,051,014 A | 4/2000 | Jang | |
| 6,059,809 A | 5/2000 | Amor et al. | |
| 6,110,201 A | 8/2000 | Quijano et al. | |
| 6,117,166 A | 9/2000 | Winston et al. | |
| 6,123,723 A | 9/2000 | Konya et al. | |
| 6,146,366 A | 11/2000 | Schachar | |
| 6,162,208 A | 12/2000 | Hipps | |
| 6,162,245 A | 12/2000 | Jayaraman | |
| 6,168,614 B1 | 1/2001 | Andersen et al. | |
| 6,171,335 B1 | 1/2001 | Wheatley et al. | |
| 6,190,393 B1 * | 2/2001 | Bevier et al. | 606/108 |
| 6,200,336 B1 | 3/2001 | Pavcnik et al. | |
| 6,203,550 B1 | 3/2001 | Olson | |

(56) References Cited

U.S. PATENT DOCUMENTS

| | | |
|---|---|---|
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman et al. |
| 6,254,564 B1 | 7/2001 | Wilk et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,287,315 B1 | 9/2001 | Wijeratne et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,338,725 B1 | 1/2002 | Hermann et al. |
| 6,338,735 B1 | 1/2002 | Stevens |
| 6,348,063 B1 | 2/2002 | Yassour et al. |
| 6,350,278 B1 | 2/2002 | Lenker et al. |
| 6,352,708 B1 | 3/2002 | Duran et al. |
| 6,355,060 B1 | 3/2002 | Lenker et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 * | 9/2002 | Schreck ............... 623/2.18 |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,562,058 B2 | 5/2003 | Seguin et al. |
| 6,569,196 B1 | 5/2003 | Vesely |
| 6,572,645 B2 | 6/2003 | Leonhardt |
| 6,592,546 B1 | 7/2003 | Barbut et al. |
| 6,605,112 B1 | 8/2003 | Moll et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 * | 11/2003 | Bailey et al. .............. 623/1.24 |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,797,002 B2 | 9/2004 | Spence et al. |
| 6,821,297 B2 | 11/2004 | Snyders |
| 6,830,584 B1 | 12/2004 | Seguin |
| 6,830,585 B1 | 12/2004 | Artof |
| 6,852,116 B2 | 2/2005 | Leonhardt et al. |
| 6,866,650 B2 | 3/2005 | Stevens |
| 6,872,223 B2 | 3/2005 | Roberts |
| 6,878,161 B2 | 4/2005 | Lenker |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,911,039 B2 | 6/2005 | Shiu et al. |
| 6,929,653 B2 | 8/2005 | Strecter |
| 6,945,990 B2 | 9/2005 | Greenan |
| 6,951,571 B1 | 10/2005 | Srivastava |
| 6,986,774 B2 | 1/2006 | Middleman et al. |
| 6,989,028 B2 | 1/2006 | Lashinski et al. |
| 7,060,038 B2 | 6/2006 | Letort et al. |
| 7,105,016 B2 | 9/2006 | Shiu et al. |
| 7,147,663 B1 | 12/2006 | Berg et al. |
| 7,163,552 B2 | 1/2007 | Diaz |
| 7,264,632 B2 | 9/2007 | Wright et al. |
| 2001/0002445 A1 | 5/2001 | Vesely |
| 2001/0007956 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0093075 A1 * | 5/2004 | Kuehne ............... 623/1.15 |
| 2004/0097788 A1 | 5/2004 | Mourles et al. |
| 2004/0098112 A1 | 5/2004 | DiMatteo et al. |
| 2004/0111096 A1 | 6/2004 | Tu et al. |

(56) References Cited

U.S. PATENT DOCUMENTS

| | | |
|---|---|---|
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0148008 A1 | 7/2004 | Goodson, IV et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2005/0010287 A1 | 1/2005 | Macoviak |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0060029 A1 | 3/2005 | Le |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0131438 A1 | 6/2005 | Cohn |
| 2005/0137686 A1 | 6/2005 | Salahieh |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0187616 A1 | 8/2005 | Realyvasquez |
| 2005/0203549 A1 | 9/2005 | Realyvasquez |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2006/0004439 A1 | 1/2006 | Spenser et al. |
| 2006/0009841 A1 | 1/2006 | McGuckin et al. |
| 2006/0020319 A1 | 1/2006 | Kim et al. |
| 2006/0259134 A1 | 11/2006 | Schwammenthal et al. |
| 2007/0005131 A1 | 1/2007 | Taylor |
| 2007/0016286 A1 | 1/2007 | Herrmann et al. |
| 2007/0027518 A1 | 2/2007 | Case et al. |
| 2007/0043420 A1 | 2/2007 | Lostetter |
| 2007/0088431 A1 | 4/2007 | Bourang et al. |
| 2008/0114442 A1 | 5/2008 | Mitchell et al. |
| 2008/0228170 A1 | 9/2008 | Murray |
| 2008/0228255 A1 | 9/2008 | Rust et al. |
| 2008/0255652 A1 | 10/2008 | Thomas et al. |
| 2008/0262590 A1 | 10/2008 | Murray |
| 2008/0262596 A1 | 10/2008 | Xiao |
| 2008/0262597 A1 | 10/2008 | Xiao |
| 2008/0275542 A1* | 11/2008 | LaDuca et al. ............... 623/1.35 |

FOREIGN PATENT DOCUMENTS

| | | | |
|---|---|---|---|
| DE | 195 46 692 | | 6/1997 |
| DE | 195 46 692 | C2 | 6/1997 |
| DE | 198 57 887 | | 7/2000 |
| DE | 199 07 646 | | 8/2000 |
| DE | 10049812 | | 4/2002 |
| DE | 10049813 | | 4/2002 |
| DE | 10049814 | | 4/2002 |
| DE | 10049815 | | 4/2002 |
| EP | 0 144167 | | 6/1985 |
| EP | 0 597967 | | 12/1994 |
| EP | 0850607 | | 7/1998 |
| EP | 1057460 | | 6/2000 |
| EP | 1057459 | | 12/2000 |
| EP | 1057460 | A1 * | 12/2000 |
| EP | 1088529 | | 4/2001 |
| EP | 0937439 | B1 | 9/2003 |
| EP | 1340473 | | 9/2003 |
| EP | 1356793 | | 10/2003 |
| EP | 0819013 | | 6/2004 |
| EP | 1472996 | | 11/2004 |
| EP | 1229864 | B1 | 4/2005 |
| FR | 2788217 | | 12/1999 |
| GB | 1 268 484 | | 3/1972 |
| GB | 2056023 | | 3/1981 |
| SU | 1271508 | | 11/1986 |
| WO | 91-17720 | | 11/1991 |
| WO | 92-17118 | | 10/1992 |
| WO | 93-01768 | | 2/1993 |
| WO | WO 93/15693 | | 8/1993 |
| WO | WO 95/04556 | | 2/1995 |
| WO | WO 95/29640 | | 11/1995 |
| WO | WO 96/14032 | | 5/1996 |
| WO | WO 98/14137 | | 4/1998 |
| WO | 98-29057 | | 7/1998 |
| WO | WO 98/36790 | | 8/1998 |
| WO | 99/12483 | | 3/1999 |
| WO | 99-33414 | | 7/1999 |
| WO | 99-40964 | | 8/1999 |
| WO | 99-47075 | | 9/1999 |
| WO | WO 00/09059 | | 2/2000 |
| WO | 00-41652 | | 7/2000 |
| WO | 00-47139 | | 8/2000 |
| WO | WO 00/44308 | | 8/2000 |
| WO | WO 00/44313 | | 8/2000 |
| WO | WO 00/47136 | | 8/2000 |
| WO | WO 00/67661 | | 11/2000 |
| WO | WO 01/05331 | | 1/2001 |
| WO | WO 01/35870 | | 5/2001 |
| WO | 01-49213 | | 7/2001 |
| WO | 01-54625 | | 8/2001 |
| WO | 01-62189 | | 8/2001 |
| WO | WO 01/64137 | | 9/2001 |
| WO | 01-97715 | | 12/2001 |
| WO | 02/41789 | | 5/2002 |
| WO | WO 02/36048 | | 5/2002 |
| WO | 02-43620 | | 6/2002 |
| WO | 02-47575 | | 6/2002 |
| WO | 02/60352 | | 8/2002 |
| WO | 02-36048 | | 10/2002 |
| WO | WO 02/100297 | | 12/2002 |
| WO | WO 03/003943 | | 1/2003 |
| WO | WO 03/003949 | | 1/2003 |
| WO | WO 03/011195 | | 2/2003 |
| WO | 03-028592 | | 4/2003 |
| WO | 03/030776 | | 4/2003 |
| WO | 03-037227 | | 5/2003 |
| WO | 03-094793 | | 11/2003 |
| WO | WO 03/015851 | | 11/2003 |
| WO | 2004/019825 | | 3/2004 |
| WO | WO 2004/019811 | | 3/2004 |
| WO | WO 2004/023980 | | 3/2004 |
| WO | WO 2004/041126 | | 5/2004 |
| WO | WO 2004/047681 | | 6/2004 |
| WO | 2004-058106 | | 7/2004 |
| WO | 2004-089250 | | 10/2004 |
| WO | 2004-089253 | | 10/2004 |
| WO | 2004-093728 | | 11/2004 |

(56) References Cited

FOREIGN PATENT DOCUMENTS

| | | |
|---|---|---|
| WO | 2004-105651 | 12/2004 |
| WO | 2005-002466 | 1/2005 |
| WO | 2005-004753 | 1/2005 |
| WO | 2005/004753 | 1/2005 |
| WO | 2005-009285 | 2/2005 |
| WO | 2005-011534 | 2/2005 |
| WO | 2005-011535 | 2/2005 |
| WO | 2005-023155 | 3/2005 |
| WO | 2005-027790 | 3/2005 |
| WO | 2005-046528 | 5/2005 |

OTHER PUBLICATIONS

Bailey, "Percutaneous expandable prosthetic valves," In: Topol, EJ, ed. Textbook of Interventional Cardiology. Volume II. Second edition. WB Saunders, Philadelphia, 1994:1268-1276.
Babaliaros, et al., "State of the Art Percutaneous Intervention for the Treatment of Valvular Heart Disease: A Review of the Current Technologies and Ongoing Research in the Field of Percutaneous Valve Replacement and Repair," Cardiology 2007;107:87-96.
Block, et al., "Percutaneous Approaches to Valvular Heart Disease," Current Cardiology Reports, vol. 7, pp. 108-113 (2005).
Brodsky, "Percutaneous approaches to aortic valve replacement," Applications in Imaging—Cardiac Interventions, Dec. 2004, pp. 4-9.
Cribier, et al., "Percutaneous Implantation of Aortic Valve Prosthesis in Patients with Calcific Aortic Stenosis: Technical Advances, Clinical Results and Future Strategies," Journal of Interventional Cardiology, vol. 19, No. 5, Supplement 2006, pp. S87-S96.
Hanel, et al., "Complications of percutaneous aortic valve replacement: experience with the Cribier-Edwards™ percutaneous heart valve," EuroIntervention Supplements (2006), 1 (Supplement A) A3-A8.
Khambadkone, et al., "Pediatric and Congenital Heart Disease," Catheterization and Cardiovascular Interventions 62:401-408 (2004).
Khambadkone, et al., "Percutaneous Pulmonary Valve Implantation in Humans Results in 59 Consecutive Patients," Circulation, 2005;112:1189-1197.
"New Frontiers in Heart Valve Disease," Medtech Insight, vol. 7, No. 8 (Aug. 2005).
Palacios, "Percutaneous Valve Replacement and Repair, Fiction or Reality?" Journal of the American College of Cardiology, vol. 44, No. 8, 2004 pp. 1662-1663.
Ruiz, "Transcathether Aortic Valve Implantation and Mitral Valve Repair: State of the Art," Pediatric Cardiology, 26:289-294, 2005.
Chiam, et al., "Percutaneous Transcatheter Aortic Valve Implantation: Assessing Results, Judging Outcomes, and Planning Trials," JACC: Cardiovascular Interventions, vol. 1, No. 4, Aug. 2008:341-50.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Webb, et al., "Percutaneous Aortic Valve Implantation Retrograde from the Femoral Artery," Circulation (2006), 113;842-850.
Younes Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Louise Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Peter C. Block, et al, "Percutaneous Approaches to Valvular Heard Disease," Current Cardiology Reports (United States), Mar. 2005, pp. 108-113.
Georg Lutter, et al, "Percutaneous Valve Replacement: Current State and Future Prospects," Annals of Thoracic Surgery (Netherlands), Dec. 2004, pp. 2199-2206.
Sachin Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Younes Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Younes Boudjemline, et al, "Images in Cardiovascular Medicine. Percutaneous Aortic Valve Replacement in Animals," Circulation (United States), Mar. 16, 2004, 109, p. e161.
Younes Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
S. Khambadkone, et al, "Percutaneous Implantation of Pulmonary Valves," Expert Review of Cardiovascular Therapy (England), Nov. 2003, pp. 541-548.
G. O. Yonga, et al, "Percutaneous Transvenous Mitral Commissurotomy in Juvenile Mitral Stenosis," East African Medical Journal (Kenya), Apr. 2003, pp. 172-174.
Younes Boudjemline, et al, "Transcatheter Reconstruction of the Right Heart," Cardiology in the Young (England), Jun. 2003, pp. 308-311.
Y. Boudjemline, et al, "Percutaneous Valve Insertion: A New Approach," Journal of Thoracic and Cardiovascular Surgery (United States), Mar. 2003, pp. 741-742.
Sachin Khambadkone, et al, "Percutaneous Pulmonary Valve Implantation: Early and Medium Term Results," Circulation 108 (17 Supplement), Oct. 28, 2003, pg. IV-375.
Sachin Khambadkone, et al, "Percutaneous Pulmonary Valve Implantation: Impact of Morphology on Case Selection," Circulation 108 (17 Supplement), Oct. 28, 2003, p. IV-642-IV-643.
Y. Boudjemline, et al, "Percutaneous Implantation of a Valve in the Descending Aorta in Lambs," European Heart Journal (England), Jul. 2002, pp. 1045-1049.
Y. Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Philipp Bonhoeffer, et al, "Percutaneous Insertion of the Pulmonary Valve," Journal of the American College of Cardiology (United States), May 15, 2002, pp. 1664-1669.
Younes Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Younes Boudjemline, et al, "Steps Toward Percutaneous Aortic Valve Replacement," Circulation (United States), Feb. 12, 2002, pp. 775-778.
Y. Boudjemline, et al, "The Percutaneous Implantable Heart Valve," Progress in Pediatric Cardiology (Ireland), 2001, pp. 89-93.
Y. Boudjemline, et al, "Percutaneous Aortic Valve Replacement: Will We Get There?" Heart (British Cardiac Society) (England), Dec. 2001, pp. 705-706.
Y. Boudjemline, et al, "Percutaneous Implantation of a Biological Valve in Aortic Position: Preliminary Results in a Sheep Study," European Heart Journal 22, Sep. 2001, p. 630.
Y. Boudjemline, et al, "Stent Implantation Combined with a Valve Replacement to Treat Degenerated Right Ventricle to Pulmonary Artery Prosthetic Conduits," European Heart Journal 22, Sep. 2001, pp. 355.

(56) References Cited

OTHER PUBLICATIONS

P. Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

P. Bonhoeffer, et al, "Transcatheter Implantation of a Bovine Valve in Pulmonary Position: A Lamb Study," Circulation (United States), Aug. 15, 2000, pp. 813-816.

Z. Saliba, et al, "Treatment of Obstructions of Prosthetic Conduits by Percutaneous Implantation of Stents," Archives des Maldies du Coeur et des Vaisseaux (France), 1999, pp. 591-596.

P. Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.

G. O. Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

G. O. Yonga, et al, "Percutaneous Balloon Mitral Valvotomy: Initial Experience in Nairobi Using a New Multi-Track Catheter System," East African Medical Journal (Kenya), Feb. 1999, pp. 71-74.

G. O. Yonga, et al, "Percutaneous Transluminal Balloon Valvuloplasty for Pulmonary Valve Stenosis: Report on Six Cases," East African Medical Journal (Kenya), Apr. 1994, pp. 232-235.

Georg Lutter, et al, "Percutaneous Aortic Valve Replacement: An Experimental Study. I. Studies on Implantation," The Journal of Thoracic and Cardiovascular Surgery, Apr. 2002, pp. 768-776.

* cited by examiner

SYSTEM AND METHOD FOR IMPLANTING A REPLACEMENT VALVE

CROSS-REFERENCE TO RELATED APPLICATION

This application is a divisional of U.S. patent application Ser. No. 10/127,969, filed, Apr. 23, 2002 now U.S. Pat. No. 8,721,713.

FIELD OF THE INVENTION

This invention relates to a system for the percutaneous implantation of a biological venous valvular replacement for a human valve.

BACKGROUND OF THE INVENTION

There exists a need in the medical field for an improved system for carrying out the percutaneous implantation of biological venous valvular replacements for human valves and in particular cardiac valves. Up until recently, many valves such as heart valves had to be replaced surgically. Accordingly, the patients were exposed to all the potential dangers of major surgery.

Recently, procedures have been devised for implanting biological valves harvested from animals percutaneously into humans to replace damaged or malfunctioning valves. Andersen et al. in U.S. Pat. No. 5,840,081 describes a system for carrying out such a procedure. In Andersen et al., a biological cardiac valve is mounted upon the expandable stent of a catheter. The assembly is crimped onto the balloon section of the catheter and a protective cap is placed over the package. The catheter is then passed through a body lumen into a predetermined site within the heart. The package is then moved out of the cap and is positioned in the implantation site using well known positioning techniques. The balloon is inflated causing the stent with the replacement valve attached thereto to expand thus implanting the valve within the desire site.

The Andersen et al. type system works well in practice in that it can be carried out in a relatively short period of time when compared to surgical procedures and the risk to the patient is considerably reduced. However, the biological prosthesis that include the venous valvular replacement and the stent tends to be relatively bulky and thick even when tightly compressed against the deflated balloon and thus sometimes difficult to move through the body lumen into the implantation site. Most catheters in present day use can not deliver the necessary torque to guide the prosthesis through the body lumen, particularly where there is a relatively tight bend in the path of travel. In addition, most of the catheters that are equipped with protective caps do not possess the rigidity needed to hold the prosthesis in the desired location as the balloon is cleared for inflation.

SUMMARY OF THE INVENTION

It is therefore an object of the present invention to improve percutaneous deliver systems for placing a biological venous valvular replacement for a defective valve within an implantation site.

A further object of the present invention is to improve the steerability of a balloon catheter used to implant a biological valve percutaneously in a patient.

A still further object of the present invention is to more accurately place a biological valve prosthesis with a desired implantation site.

Another object of the present invention is to provide a more compact system for percutaneously inserting a biological replacement valve into an implantation site.

These and other objects of the present invention are attained by a system for percutaneously inserting a biological venous valvular replacement for a defective valve within a patient through a body lumen. The system includes a balloon catheter upon which a collapsable stent containing a venous valvular replacement is mounted in a collapsed condition upon the deflated balloon. A protective shield is placed over the balloon and the replacement valve unit. The shield is movable from a closed position over the balloon to a fully opened position without having to axially displace the balloon so that the balloon can be inflated to expand the stent and accurately implant the replacement valve. A central lumen formed of a stainless steel tube passes through the catheter to provide a one to one torque ratio between the proximal end of the catheter and its distal end. The wall thickness of the venous valvular replacement is reduced from its original size by between 50% and 90% to provide for a more compact replacement package when the package is collapsed upon the uninflated balloon.

BRIEF DESCRIPTION OF THE DRAWING

For a better understanding of these and other objects of the invention, reference will be made to the following detailed description of the invention which is to be read in association with the accompanying drawing, wherein.

DETAILED DESCRIPTION OF THE INVENTION

Figure 1:
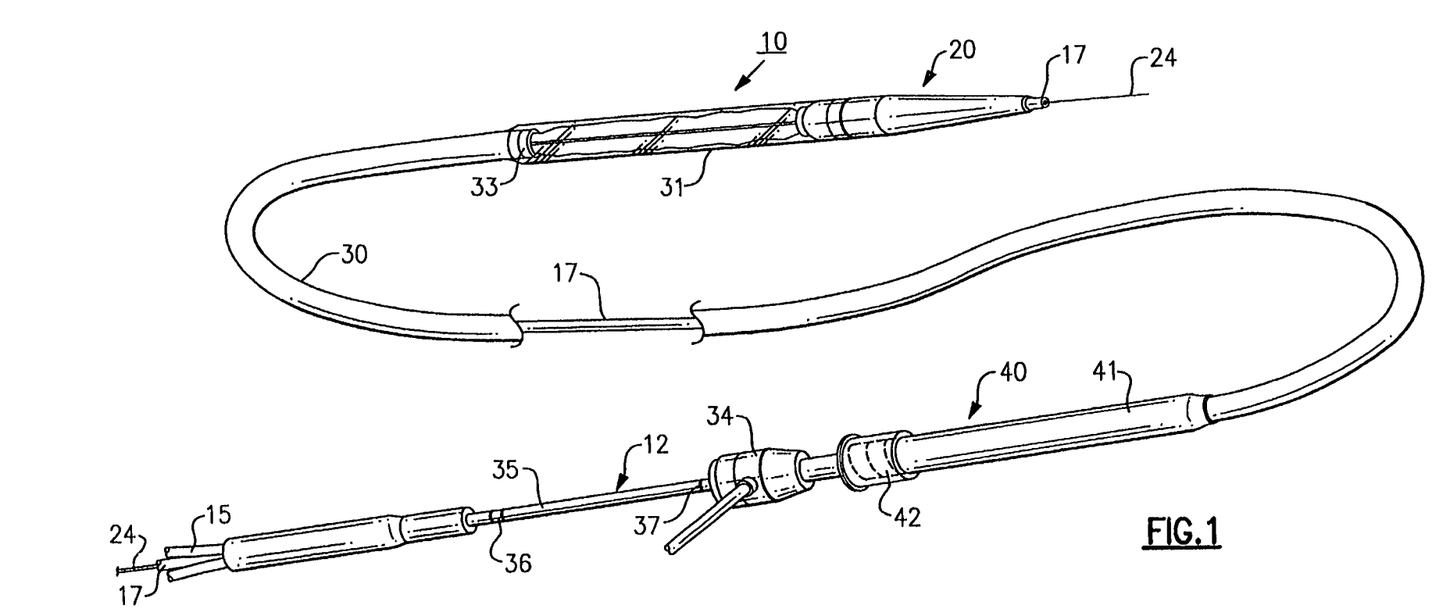
FIG. 1 is a perspective view illustrating a delivery system embodying the teachings of the present invention for the percutaneous insertion and implantation of a biological replacement valve within a patient.
Figure 2:
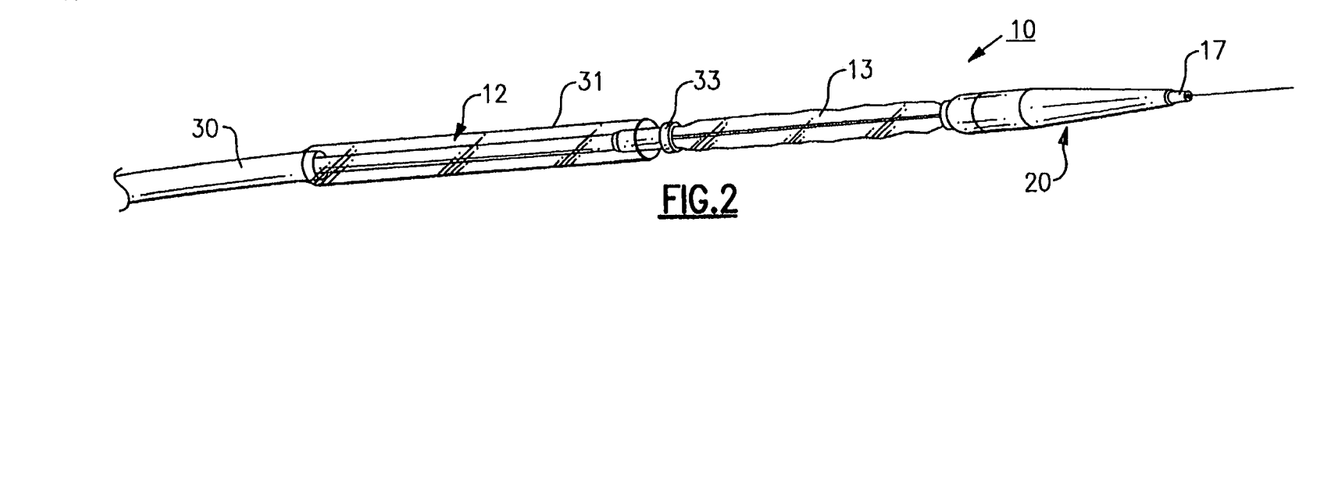
FIG. 2. is a partial perspective view illustrating the distal end of the system shown in FIG. 1 with its protective shield moved back away from the balloon section of the system.

FIGS. 1 and 2 illustrate a system, generally referenced 10, for percutaneous insertion and implantation of a biological venous valvular replacement for a defective or malfunctioning valve. The system includes an elongated balloon catheter 12 having an inflatable balloon 13 joined to the distal end of the catheter. The balloon is connected in fluid flow communication with a lumen 15 through which the balloon is inflated or deflated in a manner well known in the art. Preferably the balloon is inflated using a radio-opaque fluid. Although a single balloon is shown in the present embodiment of the invention, it should be obvious to one skilled in the art that a plurality of balloons in various configurations may be employed in the practice of the present invention.

The catheter further includes a centrally located lumen 17 that passes through the entire length of the catheter from its proximal end to its distal end. The central lumen, unlike other catheter lumens employed in the prior art, is formed from a length of stainless steel tubing. A pointed nose cone 20 is affixed to the distal end of the tubing and the rear section 21 of the nose cone is secured to the front part of the balloon. The distal end of the central lumen 17 opens to the surrounding ambient at one end through the front of the nose cone and at the other end through the rear section of the catheter as illustrated in FIG. 1.

A thin guide wire 24 passes through the central lumen which is used in a conventional manner to guide the catheter into the implantation site.

It has been found that when a stent containing a biological valve is mounted upon the balloon of a catheter, the package tends to become overly large and clumsy to maneuver. Accordingly, maneuvering of the catheter through a vein or artery to the implantation site becomes difficult, particularly where the catheter has to be conducted through a number of bends along the intended path of travel. Conventional catheters and the lumens ruing there-through are fabricated from plastic materials that tend to twist when a torque is applied to the proximal or steering end of the device. This twisting adversely effects the steering control at the distal end of the catheter making it difficult to direct the catheter around any bends in the intended path of travel and accurately place the replacement package in the implantation region. The stainless steel tube running down the center of the present catheter is designed to provide the catheter with a 1 to 1 torque ratio between the proximal end of the catheter and its distal end. This in turn, enhances the steerability of the catheter as well as providing the user with the ability to more easily push the catheter along the desired path of travel. It has been found that a stainless steel tube having an inside diameter of about 0.039" will provide the above noted desired properties while at the same time providing the catheter with sufficient flexibility to pass readily through bent regions along the path of travel. This, along with the contoured nose cone, enables the user to rapidly guide the catheter into a desired implantation site and thus considerably shorten the implantation procedure when compared to similar systems used in the art.

An elongated sheath 30 is placed over the catheter. A close running fit is provided between the sheath and the catheter so that the sheath can slide easily over the body of the catheter. A protective shield 31 is attached to the distal end of the sheath so that the shield can be repositioned by simply moving the sheath over the catheter. In assembly, the shield is movable between a fully closed position as illustrated in FIG. 1 wherein the balloon and the replacement package are protectively enclosed and a fully opened position as illustrated in FIG. 2 wherein the balloon is cleared for inflation. An annular stop 33 is mounted on the catheter adjacent to the back edge of the balloon section. The stop is arranged to arrest the forward motion of the sheath once the shield reaches a fully closed position insuring that the shield will not ride over the nose cone.

The proximal end of the sheath contains a cylindrical flange 34 by which aids the operator to manually slide the sheath over the catheter body to open or close the protective shield. The distal end 35 of the catheter passes out of the sheath through the flange and extend back a distance that is greater than the axial length of the shield. Indicator marks 36 and 37 are placed on the extended length of the catheter for informing the operator when the shield is located in either the open or the closed position.

A cylindrical fluid barrier 40 is slidably mounted upon the proximal end of the sheath. The barrier includes a tubular body section 41 and a radially extended end flange 42. The outside diameter of the body section is about equal to that of the protective shield. In practice, once the balloon shield has passed into the body lumen through the physician's incision, the body of the fluid barrier is passed into the body lumen through the incision and the flange is placed in contact against the incision opening. Once inserted, the barrier restricts the flow of body fluid through the incision opening while, at the same time, allowing the sheath and the catheter to be advanced and maneuvered within the body lumen into the implantation site.

As will be further explained below, the prosthetic device made up of an expandable stent and a biological venous valvular replacement is mounted in a collapsed state upon the balloon section of the catheter. The replacement is preferably has been harvested from the jugular vein of an animal, such as a cow, and is secured to the inside of the stent. Initially, the sheath is pulled back along the catheter to expose the collapsed balloon and the prosthetic device is passed over the balloon and crimped tightly onto the balloon to establish a compact low profile package. The sheath is then moved forward along the catheter to place the shield over the package to protect it during insertion. Once the package is positioned within the insertion site the shield again is moved back over the stationary body of the catheter as explained above and the balloon is inflated to implant the biological replacement within the site.

Figure 3:
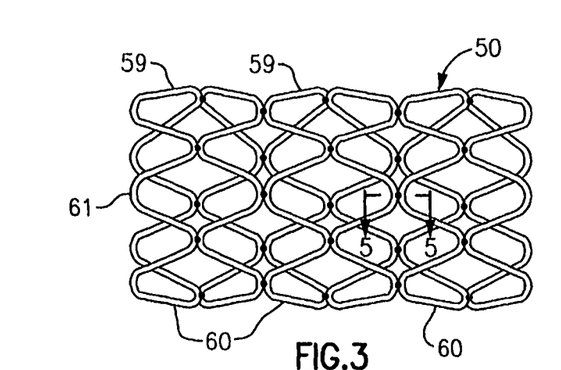
FIG. 3 is an enlarged side elevation of an expanded stent used in the practice of the present invention.

Turning more specifically to FIGS. 2-5, there is illustrated a stent 50 that is particularly well suited for use in the present system. A biological venous valvular replacement 51 for a defective valve is carried inside of the stent. Although the present valve replacement is ideally suited for percutaneous implantation of a pulmonary valve, it should clear that the present system can be used in a number of similar applications without departing from the teachings of the invention. As illustrated in FIG. 3, the biological replacement unit 51 includes a section of vein 55 that contain a valve 56. As will be explained below in further detail the venous valvular replacement is attached to the stent by means of sutures 58.

The present expandable stent includes a series of fine wire ribbon sections, each designated 60 that are joined together to create a tubular or cylindrical member. The wire stand 59 of each section is fabricated of a soft, highly malleable metal alloy that has been fully annealed to remove as much of its spring memory as possible. Preferably the wire material is fabricated of an alloy consisting of about 90% platinum and 10% iridium that has a tensile strength of between 150,000 psi and 175,000 psi. Although a platinum iridium wire is preferred for use in the present stent, other alloys having similar properties such as a gold nickle alloy may also be employed. Prior to winding the wire ribbon sections into a cylindrical shape, each section is formed so that it contains a series of alternating sinusoidal bends 61. The sections are formed by winding the strand of wire between rows of vertical pins projecting from the surface of a flat substrate. The strand is then wound about the pins in alternate rows to create a sinusoidal shaped ribbon section having a desired number of bends and a free length of wire is located at each end of the ribbon section.

Each ribbon section is next wound into a cylinder and the cylinders are then placed in axial alignment so that the apex of each bend section is located in close proximity with the apex of a bend section on an adjacent ribbon section. The adjacent bends are then welded together to cojoin the ribbon section in assembly. Although not shown, the free ends of the adjacent cylindrical ribbon sections, in turn, are bent into parallel overlapping alignment and are cojoined using similar welds.

Figure 5:
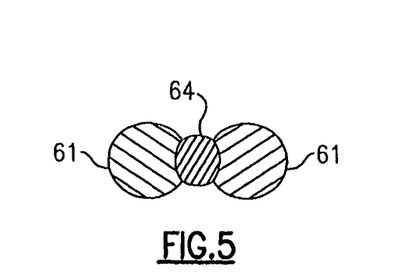
FIG. 5 is an enlarged section taken along lines 4-4 in FIG. 2.

Referring to FIG. 5, there is illustrated a typical weld joint 64 used in the practice of the present invention. Each weld is formed so that it lies inside the boundaries of the cylindrical stent as described by the inside diameter and outside diameter of the stent. Accordingly, the welds do not protrude beyond the boundaries of the wire cylinder into regions where rough edges of the welds might come in contact with the tissue of the biological valve replacement thereby preventing the tissue from becoming damaged during insertion and implantation.

A stent of the construction and configuration as herein describe has extremely good flexibility, dimensional stability, very smooth surfaces, a low profile when collapsed and an immunity to fatigue and corrosion. As should be evident the length of the stent can be varied by varying the number of ribbon sections that are utilized. By the same token, the working range of the stent between its fully collapsed condition and it fully expanded condition can also be varied by varying the number of bends in each of the ribbon sections. As can be seen each stent can be tailored for insertion into a particular body site to provide for the most effective implantation of the biological valve which is attached to the stent.

Because of the stent construction there is very little or no axial deformation of the stent as it is radially expanded or collapsed. Another feature of the present stent is its ability to be reconfigured even after implantation without adversely effecting the stents performance. This feature is important in cases where a valve has been implanted in a growing child. Rather than replacing a valve periodically during the growth period, the supporting stent can be simply reconfigured to accommodate for growth using a percutaneously introduced balloon catheter for re-engaging the stent to reconfigure the stent so that it will conform to the changes in the implantation site produced by growth.

Figure 4:
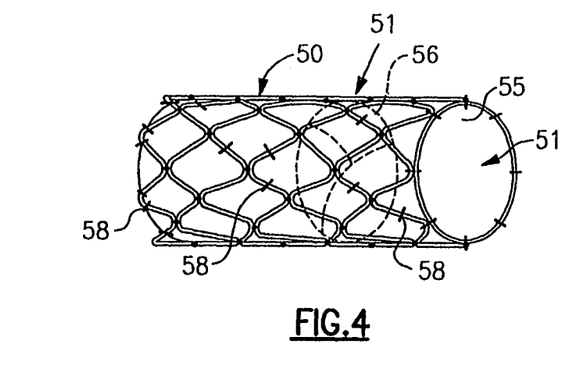
FIG. 4 is a perspective view of the stent with a biological replacement valve unit mounted inside the stent.
Figure 6:
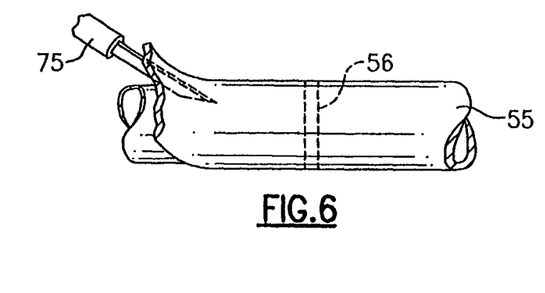
FIG. 6 is a side elevation illustrating a biological replacement valve suitable for use in the present invention as the wall thickness of the vein which supports the valve is being reduced.

As illustrated in FIG. 4, the stent is initially expanded to a desired diameter which generally conforms to the body vessel configuration at the implantation site. Next, as illustrated in FIG. 6, the vein section of the valve is trimmed to a desired length conforming to the length of the stent with the valve 56 being located in about the mid-region of the stent. In addition, the wall of the vein 56 is reduced in thickness to between 50% to 90% of its original thickness to considerably reduce the size of the valve package when the stent is collapsed over the balloon prior to insertion. It has been found that the jugular vein of a bovine animal is formed by layers of tissue that can be readily peeled back using a sharp instrument 75. The layers can be removed without destroying the integrity of the vein structure or its ability to function in a replacement prosthesis. The wall of the vein is trimmed so that its outside diameter about matches the inside diameter of the expanded stent. The vein is then passed into the expanded stent and the vein sutured to the stent as illustrated in FIG. 3. The sutures are arranged to support the vein in a fully opened circular configuration within the expanded stent.

Once the prosthesis has been sutured in place, it is passed over the balloon section of the catheter and the stent is collapsed tightly against the balloon to provide a more compact than normal package that can more easily be delivered through a body lumen into an implantation site when compared to similar devices employing bovine or eqvine biological valves replacements.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A method of percutaneously implanting a heart valve assembly, the method comprising:
    advancing the heart valve assembly crimped on a collapsed inflatable balloon of an elongated catheter of a delivery system to an implantation site, the inflatable balloon comprising a distal end directly connected to a contoured nose cone at a distal end of the elongated catheter; and
    expanding the inflatable balloon to implant the heart valve assembly at the implantation site;
    wherein the contoured nose cone has a profile that radially extends beyond a heart valve assembly crimped on the inflatable balloon.

2. The method of claim 1, wherein the contoured nose cone is configured to slide along an internal surface of a blood vessel.

3. The method of claim 2, wherein the contoured nose cone comprises a leading tip portion having a diameter that increases in a proximal direction.

4. The method of claim 3, wherein the leading tip portion is substantially frusto-conical.

5. The method of claim 1, wherein the delivery system further comprises a sheath comprising a protective shield at a distal end of the sheath, the sheath being configured to slidably receive the elongated catheter.

6. The method of claim 5, wherein the protective shield comprises a distal end portion sized and shaped to afford engagement with a proximal end portion of the nose cone.

7. The method of claim 5, wherein the balloon and protective shield are sized and shaped to afford crimping of a heart valve assembly onto the balloon so that the heart valve may be positioned between the balloon and the shield.

8. The method of claim 7, further comprising moving the sheath and protective shield between
    a first closed position with a distal end portion of the shield being engaged with a proximal end portion of the nose cone and a heart valve assembly positioned between the shield and the balloon and
    a second open position with the shield sufficiently distanced from the heart valve assembly to permit expansion of the heart valve assembly by expansion of the balloon.

9. The method of claim 1, wherein the inflatable balloon is connectable to a device for inflating and deflating the balloon.

10. The method of claim 1, wherein the elongated catheter and the contoured nose cone collectively define a passageway for slidably receiving a guide wire.

11. A method of percutaneously implanting a heart valve assembly, the method comprising:
    advancing the heart valve assembly crimped on a collapsed inflatable balloon of an elongated catheter of a delivery system to an implantation site, the inflatable balloon comprising a distal end directly connected to a contoured nose cone at a distal end of the elongated catheter; and
    expanding the inflatable balloon to implant the heart valve assembly at the implantation site;
    wherein the delivery system further comprises a sheath configured to slidably receive the elongated catheter, the sheath comprising a protective shield at a distal end of the sheath;
    wherein the protective shield comprises a distal end portion sized and shaped to afford engagement with a proximal end portion of the nose cone.

12. The method of claim 11, further comprising moving the sheath and protective shield between a first closed position with a distal end portion of the shield being engaged with a proximal end portion of the nose cone and a heart valve assembly positioned between the shield and the balloon and a second open position with the shield sufficiently distanced from the heart valve assembly to permit expansion of the heart valve assembly by expansion of the balloon.

13. The method of claim 11, wherein the contoured nose cone is configured to slide along an internal surface of a blood vessel.

14. The method of claim 11, wherein the contoured nose cone comprises a leading tip portion having a diameter that increases in a proximal direction.

15. The method of claim 14, wherein the leading tip portion is substantially frusto-conical.

16. The method of claim 11, wherein the inflatable balloon is connectable to a device for inflating and deflating the balloon.

17. The method of claim 11, wherein the elongated catheter and the contoured nose cone collectively define a passageway for slidably receiving a guide wire.

* * * * *